(12) United States Patent
West

(10) Patent No.: US 6,579,354 B1
(45) Date of Patent: Jun. 17, 2003

(54) ACIDIC COPPER—ALUMINUM NITRATE WOOD PRESERVATIVE

(76) Inventor: Michael Howard West, 54 S. Crockett Rd., Senatobia, MS (US) 38668

( * ) Notice: Subject to any disclaimer, the term of this patent is extended or adjusted under 35 U.S.C. 154(b) by 0 days.

(21) Appl. No.: 10/340,959

(22) Filed: Jan. 13, 2003

(51) Int. Cl.$^7$ ................................................ A01N 59/20
(52) U.S. Cl. ................................ 106/18.32; 106/15.05; 424/630; 424/633; 424/682
(58) Field of Search .......................... 106/15.05, 18.32; 424/630, 633, 682

(56) References Cited

U.S. PATENT DOCUMENTS

| | | | | |
|---|---|---|---|---|
| 5,478,598 A | * | 12/1995 | Shiozawa | 427/297 |
| 5,846,305 A | * | 12/1998 | Payzant | 106/18.3 |
| 5,874,025 A | * | 2/1999 | Heuer et al. | 252/383 |
| 6,352,583 B1 | * | 3/2002 | Goettsche et al. | 106/18.32 |
| 6,441,016 B2 | * | 8/2002 | Goettsche et al. | 514/383 |

FOREIGN PATENT DOCUMENTS

| | | | |
|---|---|---|---|
| JP | 2001-15404 | * | 6/2001 |

* cited by examiner

*Primary Examiner*—Anthony J. Green

(57) ABSTRACT

The present invention relates to a water soluble acidic copper wood preservative composition with good copper fixation, and without environmental challenged hexavalent chromium. The composition comprises a water soluble acidic copper pesticide combined with aluminum nitrate wherein the weight ratio of aluminum nitrate to copper ranges from 1 to 10 to 10 to 1.

1 Claim, No Drawings

ACIDIC COPPER— ALUMINUM NITRATE WOOD PRESERVATIVE

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

The field of endeavor to which this invention pertains relates to the preservation of wood with water soluble acidic copper pesticides, and to compositions containing acidic copper and aluminum nitrate in weight ratios ranging from 1 to 10 to 10 to 1. Problems in the prior art with acidic copper wood preservation include difficulty in achieving copper fixation. Fixation has been historically achieved by combining chromates with the acidic copper. Now, there is increasing environmental pressure against the use of chromates, and this solution to copper fixation is no longer viable.

Acidic copper wood preservatives include both inorganic and organic salt of the metal. These are usually prepared by reacting an acid with copper metal, copper oxide, copper carbonate, or copper hydroxide. Copper salts of the stronger acids are more water soluble, and more difficult to fix in the wood. Aluminum nitrate is a well known chemical; but it has not been used in commercial wood preservation.

BRIEF SUMMARY OF THE INVENTION

The claimed invention relates to an acidic copper wood preservative composition with good copper fixation, and without chromates. My composition comprises a water soluble acidic copper pesticide combined with aluminum nitrate wherein the weight ratio of aluminum nitrate to copper ranges from 1 to 10 to 10 to 1. The existing problem solved by my invention consists of the elimination of environmental problems associated with the use of hexavalent chromium.

DETAILED DESCRIPTION OF THE INVENTION

The preferred embodiment of my invention uses copper dissolved with propionic acid, and combined with aluminum nitrate. The preferred copper source is copper hydroxide, and the preferred aluminum nitrate is the technical 60% material in water. The exact amount of propionic acid needed to dissolve the copper depends upon the amount of aluminum nitrate used, and its excess nitric acid . Hence, it is preferred propionic acid be added to the copper and aluminum nitrate mix until the copper just dissolves. The preferred weight ratio of aluminum nitrate to copper is near 1 to 1; but may vary widely. Example 1 illustrates the preparation of the preferred embodiment of my composition invention wherein the ingredients were added in the order listed with vigorous mixing. It will be obvious to those skilled in the art that concentrate wood preservatives can be produced in similar manner.

EXAMPLE 1

| | |
|---|---|
| Water | 98.70 pbw |
| Technical copper hydroxide (57.3% copper) | 0.44 pbw |
| Technical 60% aluminum nitrate | 0.40 pbw |
| Technical 99% propionic acid | 0.46 pbw |

The composition from Example 1 was used to treat southern yellow pine decking lumber to approximately 0.1 pounds per cubic foot copper retention. Similar decking was treated to approximately the same copper retention using copper sulfate and sodium dichromate blended in water according to American Wood Preservers Association Standard P5-95-1. Both groups of treated decking were cut to remove 4 inches from the center of each board, and the center samples retained in interior storage for future analysis. The longer pieces were exposed as typical decks for six years. At the end of this period each board was sampled from the center; and these samples, as well as samples from the interior storage, were tested for copper content. The acid copper chromate boards lost 21% copper during decking exposure. The copper- aluminum nitrate boards lost 18% copper.

It will be obvious to those skilled in the art that other pesticides and inert ingredients can be used in conjunction with the composition of my invention, just as they have been used with copper chromate compositions.

I claim:

1. A wood preservative composition which comprises a water soluble acidic copper pesticide combined with aluminum nitrate wherein the weight ratio of aluminum nitrate to copper ranges from 1 to 10 to 10 to 1.

* * * * *